(12) United States Patent
Cantlon et al.

(10) Patent No.: US 8,494,652 B2
(45) Date of Patent: Jul. 23, 2013

(54) IMPLANTABLE MEDICAL ANCHOR

(75) Inventors: Kurt Cantlon, Plano, TX (US); Tommy Cushing, Prosper, TX (US); John K. Henderson, Little Elm, TX (US); Paul Burns, Celina, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 66 days.

(21) Appl. No.: 13/204,848

(22) Filed: Aug. 8, 2011

(65) Prior Publication Data

US 2012/0035692 A1     Feb. 9, 2012

Related U.S. Application Data

(60) Provisional application No. 61/371,867, filed on Aug. 9, 2010.

(51) Int. Cl.
*A61N 1/00* (2006.01)

(52) U.S. Cl.
USPC ........................................................ 607/116

(58) Field of Classification Search
USPC .......................................................... 607/116
See application file for complete search history.

(56) References Cited

U.S. PATENT DOCUMENTS

| | | | |
|---|---|---|---|
| 5,273,053 A | 12/1993 | Pohndorf | |
| 7,831,313 B2 * | 11/2010 | Lauro | 607/126 |
| 8,229,573 B2 | 7/2012 | Chen et al. | |
| 8,301,268 B1 * | 10/2012 | Jones et al. | 607/126 |
| 2010/0312319 A1 | 12/2010 | Barker | |
| 2011/0022141 A1 | 1/2011 | Chen et al. | |
| 2011/0022142 A1 | 1/2011 | Barker et al. | |

\* cited by examiner

*Primary Examiner* — George Manuel

(57) ABSTRACT

There is disclosed various embodiments of an implantable anchor for permanently anchoring a medical lead or catheter. For instance, there is disclosed an implantable anchor including a body having a longitudinal lumen defined therein, wherein the longitudinal lumen is sized to accept a portion of the medical lead or catheter, a bending mechanism coupled to the body for bending the lead to a predetermined angle within the body, and a retaining mechanism for maintaining the predetermined angle of the bent lead within the body.

17 Claims, 13 Drawing Sheets

IMPLANTABLE MEDICAL ANCHOR

CROSS-REFERENCE TO RELATED APPLICATIONS

This application claims the benefit of U.S. Provisional Application No. 61/371,867, filed Aug. 9, 2010, which is incorporated herein by reference.

TECHNICAL FIELD

The present application is generally related to an implantable medical anchor for anchoring a lead of implantable medical device system within a patient.

BACKGROUND INFORMATION

Neurostimulation therapy is frequently associated with patients having a wide variety of diseases and disorders. In general, neurostimulation therapy works by applying an electrical current to the nerves which may be causing symptoms, such as chronic pain.

In neuromodulation systems, such as spinal cord stimulation systems ("SCS"), a thin wire or lead with electrodes at its distal end is implanted into a patient in the location to be treated, such as within the epidural space of the patient to deliver the electrical pulses to the spinal neural tissue. A pulse generator is typically implanted within a subcutaneous pocket within the patient and is electrically connected to the proximal end of the electrical lead. The pulse generator generates electrical pulses or current which stimulates the nerves around the electrodes at the treatment location.

Leads may be either paddle style or percutaneous. Paddle style leads have a relatively flat wide portion at the distal end of the lead. Flat electrodes are typically positioned on one face of the paddle leads. Percutaneous leads use cylindrical electrodes and are smaller, catheter style leads that are implanted with the aid of a special needle.

The efficacy of the electrical stimulation in facilitating the management of pain of the patient depends upon applying the electrical pulses to the appropriate neural tissue. If the leads migrate, the effectiveness of the electrical stimulation is greatly reduced.

Convention methods for affixing stimulation leads in place include suture sleeves having elastomeric gripping portions positioned around the lead. The suture sleeves are designed to be sutured in place, which in turn "anchors" or positions the lead within the patient. However, some leads are designed to stretch longitudinally as the patient moves. This longitudinal stretching reduces the diameter of the leads. A reduction in the diameter of the leads translates to less gripping by a conventional sleeve. Accordingly, it is desired to retain the stimulation lead at a relatively fixed position over time even if the diameter of the lead changes due to the movement of the patient.

SUMMARY

There is disclosed various embodiments of an implantable anchor for anchoring a medical lead. In one embodiment, the implantable anchor may include a body having a longitudinal lumen defined therein, wherein the longitudinal lumen is sized to accept a portion of the medical lead or catheter, a bending mechanism coupled to the anchor body for bending the lead to a predetermined angle within the body, a retaining mechanism for maintaining the predetermined angle of the bent lead within the body.

There is also disclosed various methods for coupling an implantable anchor to a medical lead. In one embodiment, the method may include the steps of threading a lead through a substantially straight longitudinal lumen of a suturing anchor, longitudinally positioning a suturing anchor along the lead, bending the longitudinal lumen of the suturing anchor such that the longitudinal lumen is no longer straight thereby bending the lead such that the lead is inhibited from longitudinally moving with respect to the anchor. In other embodiments, the method may also include the step of retaining the bending of the lead to prevent migration of the lead.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

BRIEF DESCRIPTION OF THE DRAWINGS

FIG. 3b is a different perspective view of the component of FIG. 3a.

FIG. 3c is a side elevational view of the component of FIG. 3a.

FIG. 3d is an end elevational view of the component of FIG. 3a.

FIG. 6a is a perspective view of one embodiment of a component of the anchor of FIG. 5a.

FIG. 6b is a perspective view of one embodiment of a component of the anchor of FIG. 5a.

FIG. 8a is a perspective view of one embodiment of a component of the anchor of FIG. 7a.

FIG. 8b is a sectional view of the component of FIG. 8a.

DETAILED DESCRIPTION

Figure 1A:
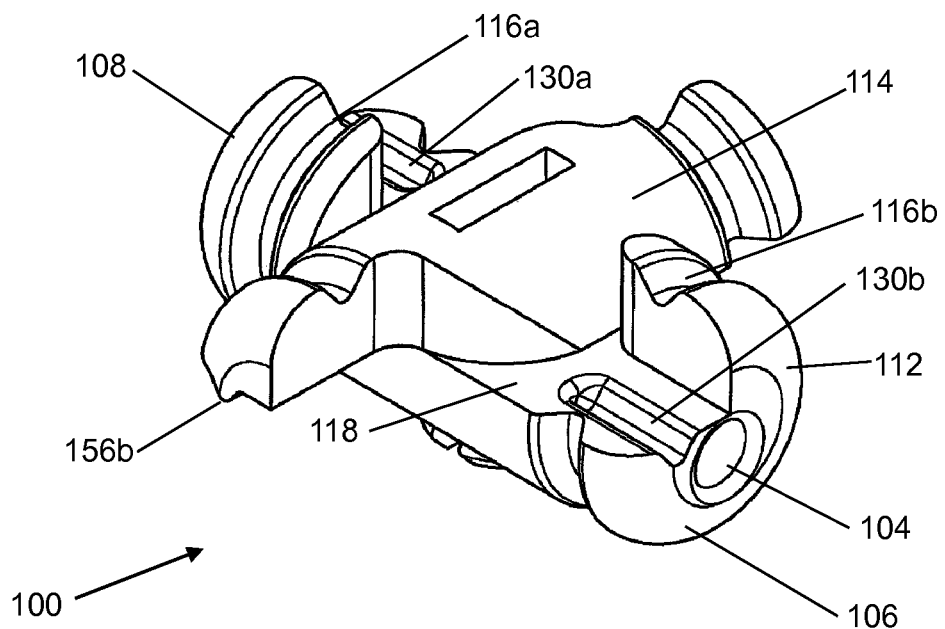
FIG. 1a is an perspective view of one embodiment of an implantable anchor in a first or unlocked configuration.

For the purposes of promoting an understanding of the principles of the present invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the inventions as described herein are contemplated as would normally occur to one skilled in the art to which the invention relates.

When directions, such as upper, lower, top, bottom, clockwise, counter-clockwise, are discussed in this disclosure, such directions are meant to only supply reference directions for the illustrated figures and for orientated of components in the figures. The directions should not be read to imply actual directions used in any resulting invention or actual use. Under no circumstances, should such directions be read to limit or impart any meaning into the claims.

Figure 1B:
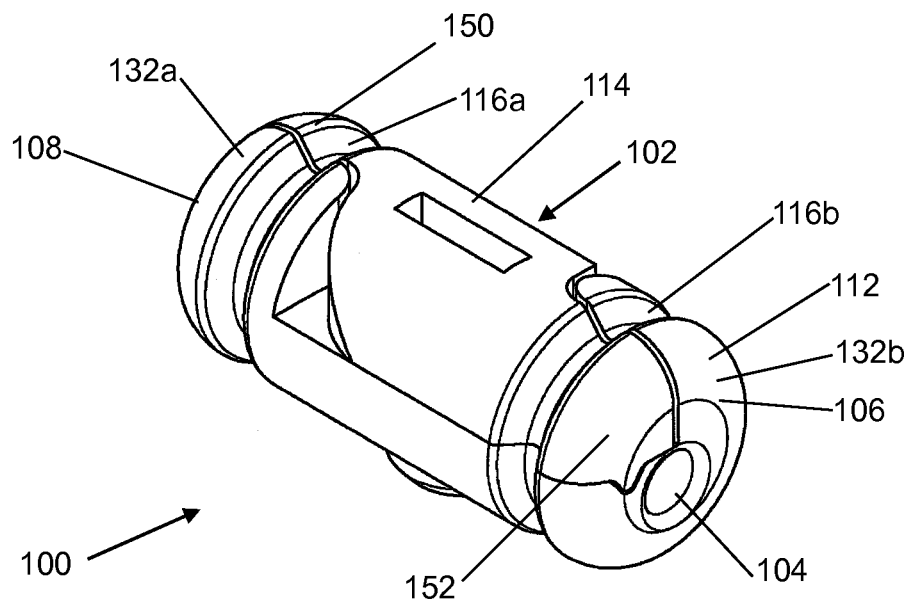
FIG. 1b is an perspective view of the anchor of FIG. 1a in a second or locked configuration.

FIG. 1a depicts an implantable anchor 100 in a first or unlocked configuration. FIG. 1b depicts the anchor 100 in a second or locked configuration. The anchor 100 may be used for anchoring an electrical lead, or other catheter (not shown) according to one representative embodiment. For the purpose of this disclosure, the term "lead" is used in a broad manner and should be interpreted to encompass both stimulation leads and infusion catheters.

Figure 13:
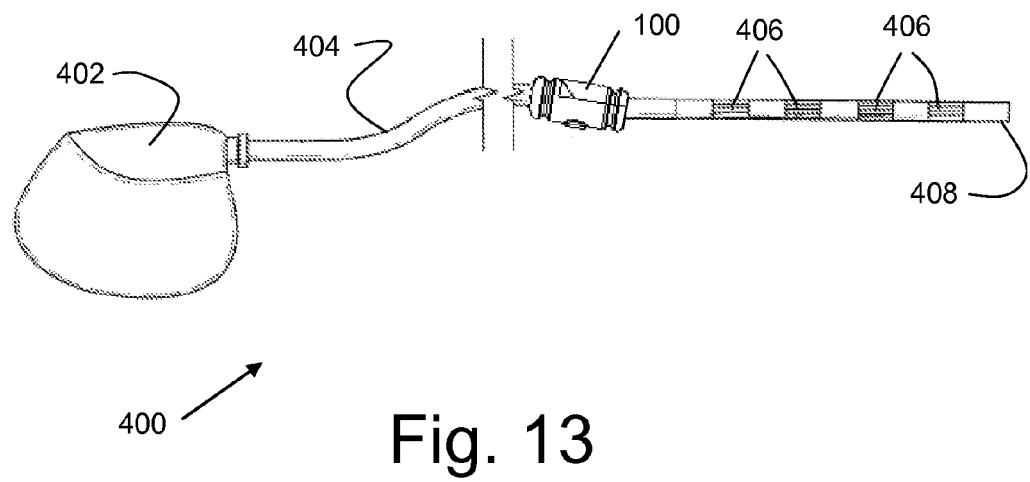
FIG. 13 is a diagram illustrating a neurostimulation system using one embodiment of the above anchors.

The anchor 100 may comprise a longitudinal body 102 having one or more longitudinal lumens defined therein. In the unlocked configuration, a lumen 104 runs longitudinally along a straight axis (i.e. linearly) from a first end 106 to a second end 108 of the longitudinal body 102. Although the lumen 104 is illustrated, any number of lumens may be used and are within the scope of the present invention. As will be explained in greater detail below, the diameter of the longitudinal lumen 104 may be sized to slidingly receive a lead of a neuromodulation system, such as a SCS system (FIG. 13). In use, therefore, one end of the lead (such as the proximal end) is intended to be threaded through the lumen 104. The anchor 100 is then slid over the lead or leads until the anchor is properly positioned along the longitudinal length of the lead or leads.

As illustrated in FIGS. 1a and 1b, the longitudinal body 102 comprises two portions: a stationary member 112 and a locking or moveable member 114 (i.e. for purposes of this disclosure, the moveable member 114 moves or rotates relative to the stationary member 112). As will be explained in detail later, when the moveable member 114 is in the open or unlocked position (as illustrated in FIG. 1a) relative to the stationary member 112, a lead may be able to freely slide through the longitudinal lumen 104. When the moveable member 114 is in the closed or locked configuration, as illustrated in FIG. 1b, the lumen 104 is no longer linear and the flexible lead is forced to bend within the anchor 100. This bending substantially inhibits the lead from freely sliding through the longitudinal lumen 104 and locks the anchor 100 longitudinally in place relative to the lead.

In some embodiments, when the anchor 100 is in the locked configuration (FIG. 1b), circumferential indents or grooves 116a and 116b are defined within the exterior wall portions of the anchor 100. The circumferential grooves 116a and 116b are defined on both the stationary member 112 and the moveable member 114. The circumferential grooves 116a-116b are designed to assist suturing of anchor 100 to tissue of the patient by allowing a portion of the suture to fit around and within the circumferential grooves 116a-116b. In other embodiments, one or more anchor holes or other similar structures (such as a plurality of circumferential rib structures) could also be provided in addition to or in place of the circumferential grooves.

Figure 2A:
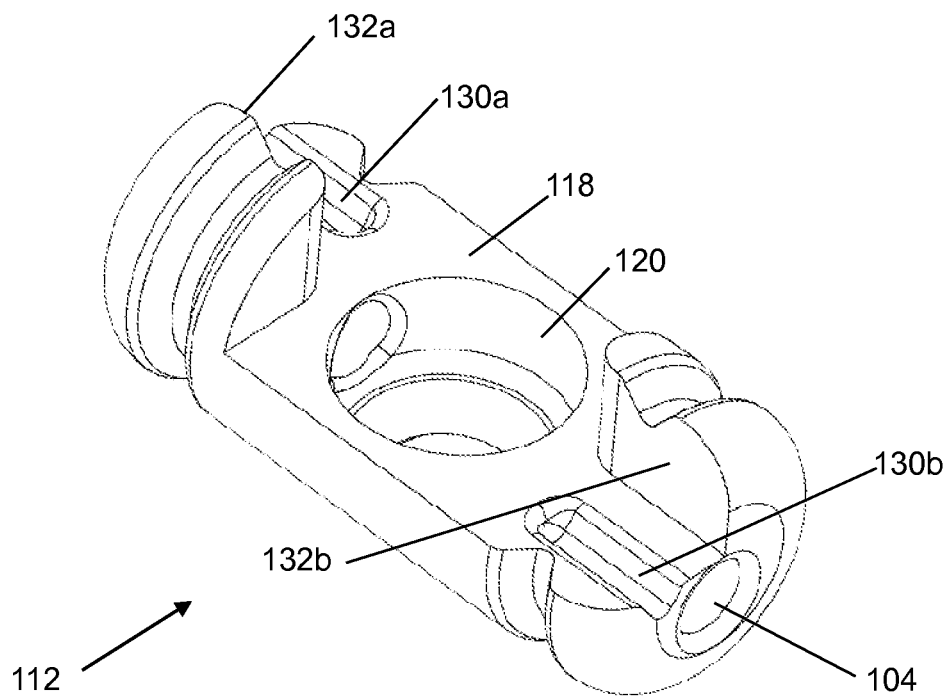
FIG. 2a is an perspective view of one embodiment of a component of the anchor of FIG. 1.
Figure 2B:
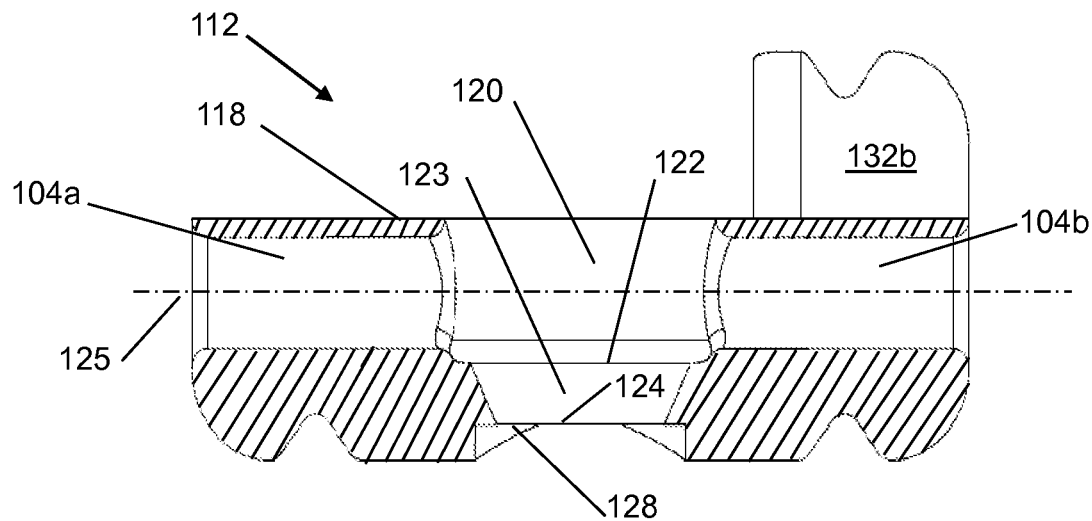
FIG. 2b is a sectional view of one embodiment of a component of the anchor of FIG. 1.

Turning now to FIG. 2a, there is illustrated the stationary member 112 of the anchor 100. FIG. 2b is a section view of the stationary member 112. In this embodiment, the stationary member 112 is partially cylindrical in shape with a portion of the cylinder above the lumen 104 removed to form a generally flat surface 118.

A transverse circular opening 120 is defined within the stationary member 112. As will be explained later, the circular opening 120 is designed to receive a portion of the moveable member 114 (FIG. 1a). The circular opening 120 forms two lumens 104a and 104b which are longitudinally aligned with each other.

FIG. 2b illustrates that the circular opening 120 runs entirely through the stationary member 112 and is transverse to the longitudinal axis 125 of the stationary member 112 and the lumens 104a-104b. At point 122, the circular opening 120 begins to gradually narrow to point 124, and then abruptly expands to form an annular shelf 128.

Turning to back to FIG. 2a, there is illustrated detents 130a and 130b which are defined on the surface 118. As will be explained in detail below, the detents 130a and 130b are designed to house and lock in place corresponding structures of the moveable member 114. In some embodiments, the detents 130a and 130b are beveled near the flat surface 118. Buttresses or stops 132a and 132b project out from the surface 118 and are designed to limit the rotation of the moveable member 114 with respect to the stationary member 112 when in the locked position.

Figure 3A:
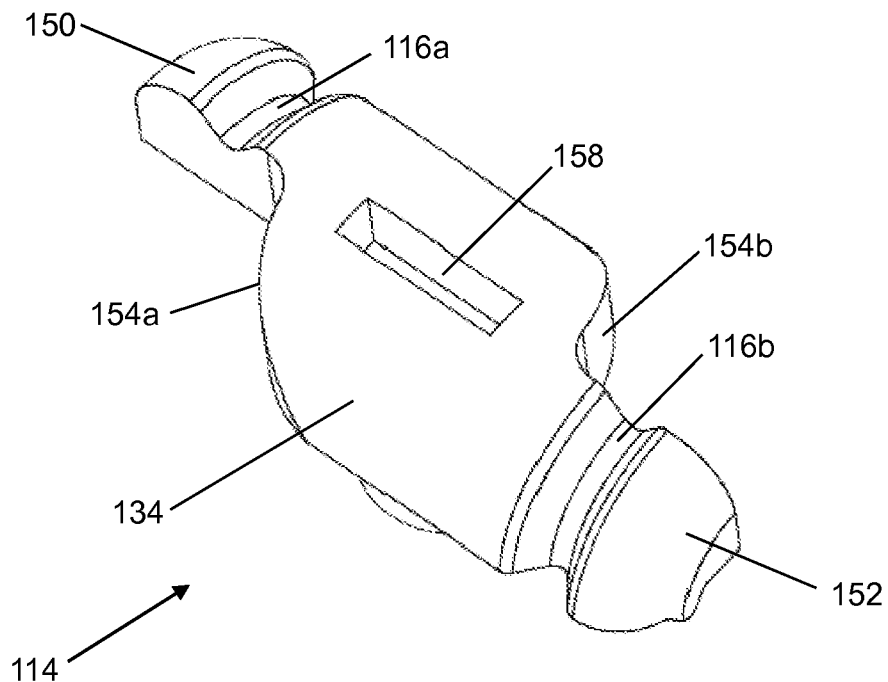
FIG. 3a is a perspective view of one embodiment of a component of the anchor of FIG. 1.
Figure 3B:
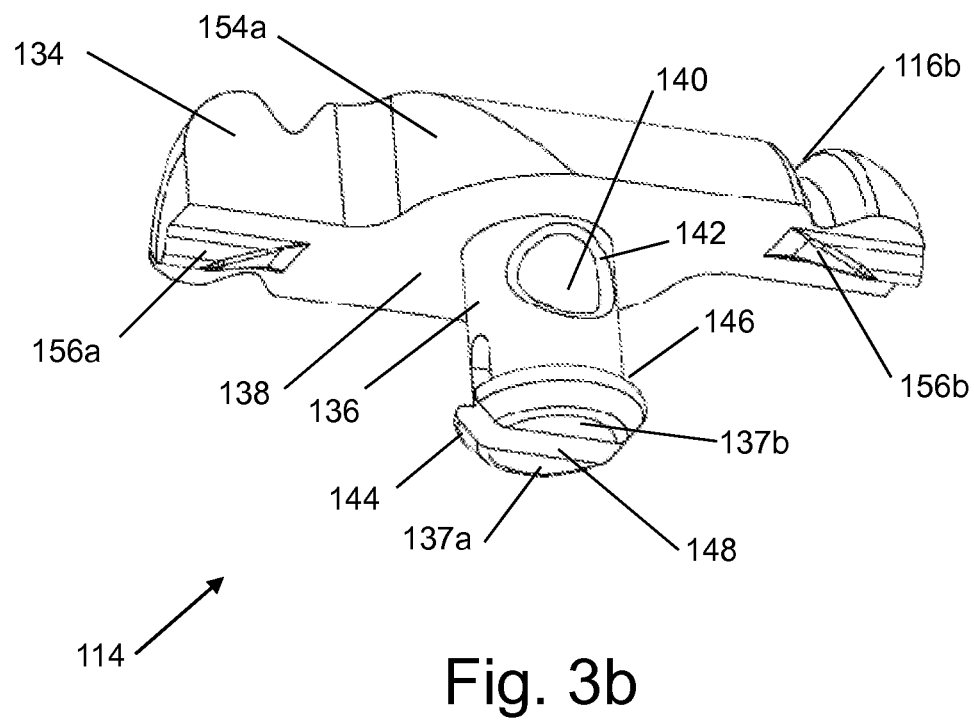
Figure 3C:
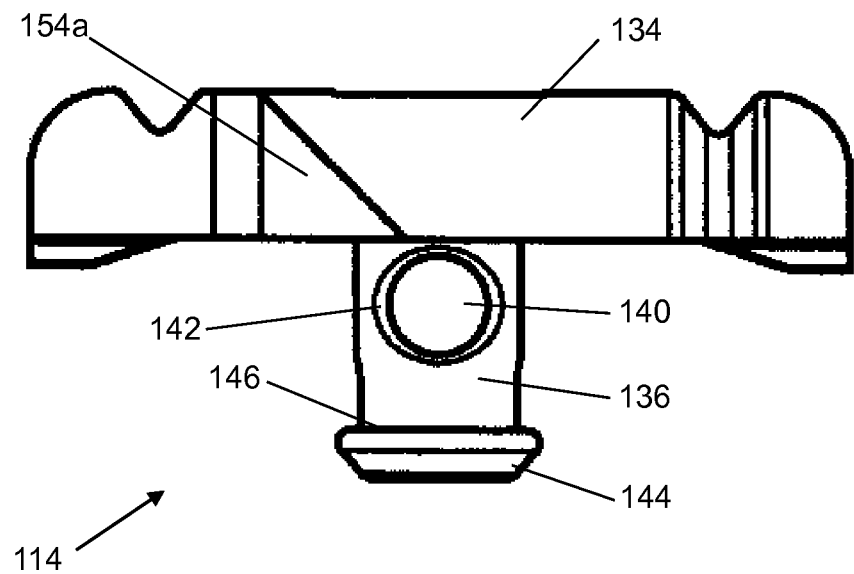
Figure 3D:
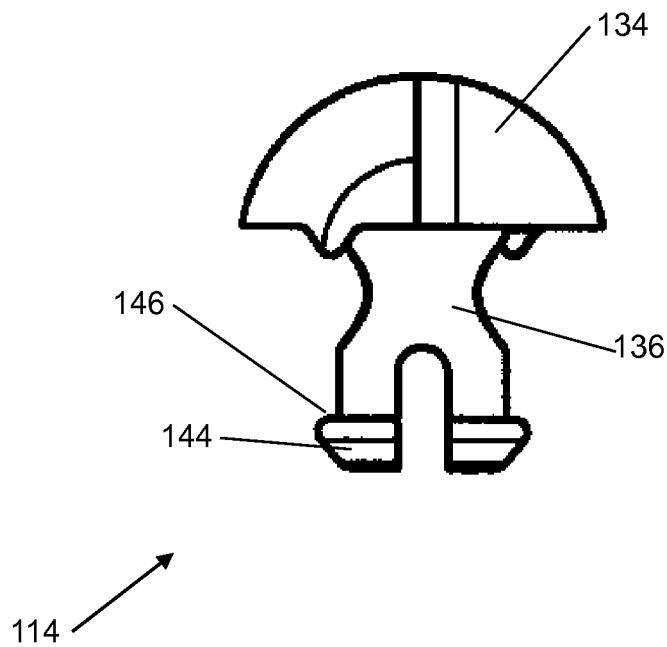

FIG. 3a is a perspective view of the moveable member 114 taken from above the member. FIG. 3b is a perspective view of the moveable member 114 taken from below the member. FIG. 3c is a side elevational view of the moveable member 114 and FIG. 3d is an end elevational view.

In certain embodiments, the moveable member 114 comprises a locking arm 134. A shaft 136 protrudes from a surface 138 of the locking arm 134 to generally form a T-member.

The shaft 136 is sized to fit within the opening 120 of the stationary member 112 (FIG. 2a). A lumen or bore 140 runs through the shaft 136. In certain embodiments, the lumen 140 is slightly beveled near the surface of the shaft 136 to form a guide or beveled edge 142 to allow for easier threading of the lead (not shown) through the lumen.

A lip 144 is formed on the end of the shaft 136 and has an upper edge 146. The lip 144 is conical in shape which allows for easier insertion of the lip 144 into the opening 120 (FIG.

2b) when the opening narrows from point 122 to point 124. A longitudinal slit 148 is also defined within the end of shaft 136. The longitudinal slit 148 splits the shaft 136 into two legs 137a and 137b. The legs 137a-137b are more flexible than the shaft and will deflect when pressed together. This deflection allows the lip 144 to narrow in diameter when compressed.

Referring now to FIG. 2b and FIG. 3b, during assembly of certain embodiments of the anchor 100, the shaft 136 is inserted into the conical section 123 of opening 120, the lip 144 will begin to narrow when it reaches point 122 of the opening 120. Upon applying additional pressure, the diameter of the lip 144 is further reduced as the legs 137a and 137b are pressed closer together. Once upper edge 146 of the lip 144 clears the point 124 of the opening 120, the lip 144 will expand laterally as the legs 137a and 137b snap back into their original positions. The annular shelf 128 abuts upper edge 146 and will keep the moveable member 114 from backing out of the stationary member 112, yet allowing the moveable member 114 to rotate with respect to the stationary member 112.

Reference should be made to FIGS. 3a through 3d while certain details of the locking arm 134 will now be discussed. The shape of the locking arm 134 allows the arm to transversely rotate with respect to the stationary member 112. In the locked position (illustrated in FIG. 1b), an end portion 150 is designed to abut the buttress 132a. Similarly, an end portion 152 is designed to abut the buttress 132b. When the anchor 100 is in the locked position, the end portions 150 and 152 are shaped to match the generally cylindrical shape of the anchor 100. Thus, they are generally quarter-round in cross-sectional shape. Furthermore, circumferential grooves are also defined on the end portions 150 and 152 such that circumferential grooves 116a and 116b completely surround the stationary member 112 and the moveable member 114 when the anchor 100 is in the locked configuration.

Curves surfaces 154a and 154b allow the locking arm 134 to transversely rotate between the buttresses 132a and 132b without causing interference with the flat surfaces of the buttresses.

Protrusions 156a and 156b extend from the surface 138. When the anchor 100 is assembled, the surface 138 of the moveable member 114 is opposed to the surface 118 of the stationary member 112. The protrusions 156a and 156b are designed to mate and fit within the detents 130a and 130b, respectively. The protrusions 156a and 156b are shaped to allow the arm 134 to be able to gradually deform when the protrusions are rotated such that they slide over the surface 118.

Referring back to FIGS. 1a and 1b, as the moveable member 114 is rotated counter-clockwise with respect to the stationary member 112, the protrusions 156a and 156b slide over the surface 118 until they reach the detents 130a and 130b. The protrusions 156a-156b will then slide into the detents 130a-130b and the moveable member 114 will be locked or retained in place as illustrated in FIG. 1b. In other embodiments (not shown), the detents may be defined in moveable member and the protrusions may be defined in the stationary member.

Buttresses 132a and 132b (FIG. 2a) inhibits the moveable member 114 from further rotation in the event that the user attempts to turn the moveable member 114 too far.

A slot 158 (FIG. 3a) or similar engaging feature may be formed on an exterior surface of the moveable member 114 to allow an instrument (not shown), such as a screwdriver, to be inserted and mate with the slot. Once the instrument is mated with the slot 158, the instrument can apply torque to the moveable member 114 to turn the moveable member 114 counter clockwise and "unlock" the moveable member 114 to an unlocked configuration as illustrated in FIG. 1a. Thus, the slot 158 allows a surgeon or other user to unlock the anchor 100. Such unlocking may be necessary to remove the anchor or adjust the longitudinal position with respect to a lead of the anchor during the surgical procedure.

Figure 4A:
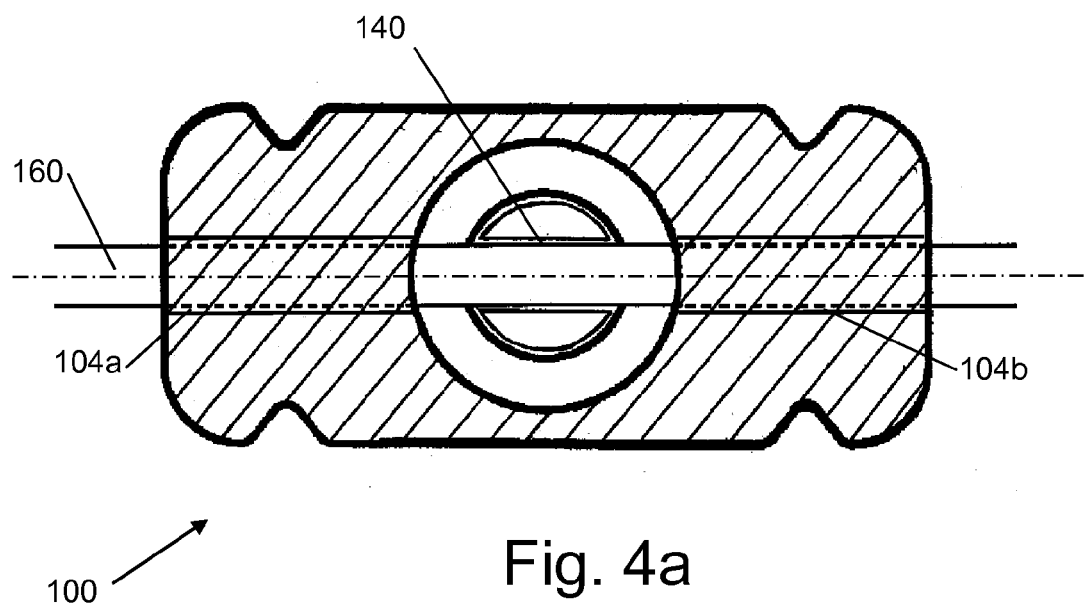
FIG. 4a is a sectional view of the anchor of FIG. 1a in an unlocked configuration.
Figure 4B:
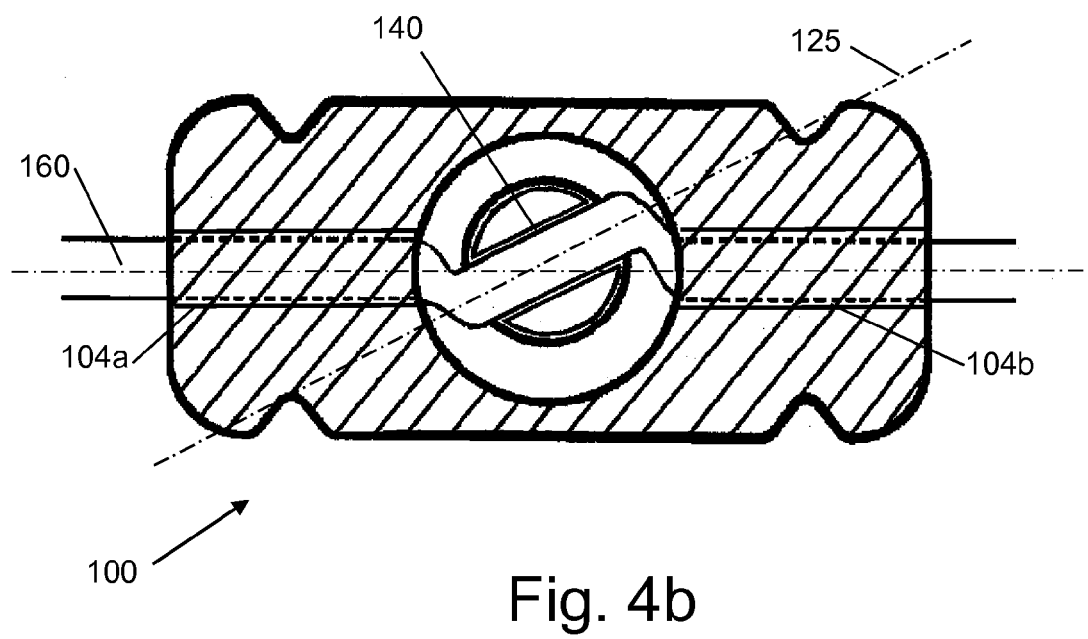
FIG. 4b is a sectional view of the anchor of FIG. 1a in a locked configuration.

Turning now to FIG. 4a, there is illustrated a sectional view of the anchor 100 in an unlocked configuration. FIG. 4b illustrates a sectional view of the anchor 100 in a locked position or configuration. FIG. 4a corresponds to the unlocked configuration presented in FIG. 1a. FIG. 4b corresponds to locked configuration of FIG. 1b. In use, the anchor 100 is initially in an unlocked configuration as illustrated in FIG. 1a and FIG. 4a. In this configuration, the lumens 104a and 104b of the stationary member 112 are linearly aligned with the lumen 140 of the moveable member 114. In other words, the longitudinal axes 121 of the three lumens 104a, 104b and 140 are identical and form one longitudinal lumen 104.

The diameters of the lumens 104a, 104b, and 140 are sized to permit the introduction of a lead 160 with little difficulty. Thus, when the moveable member 114 is in the open position or unlocked configuration, the anchor 100 may be freely moved along the lead 160. However, as illustrated in FIGS. 1b and 4b, when the moveable member 114 is rotated to the locked configuration, the lumen 140 is bent relative to the lumens 104a and 104b, thus inhibiting movement of the anchor 100 along the lead 160. Thereby, upon rotation of the moveable member 114 from an unlocked to a locked position, a bend, or kink in the lead 160 is introduced which will cause anchor 100 to hold the lead in place. The lead 160, therefore, is substantially inhibited from slipping through the anchor 100 along its longitudinal axis.

Note that when the anchor 100 is in the locked position or configuration, the longitudinal axis 125 of the lumen 140 has been rotated to a predetermined angle relative to the lumens 104a and 104b. Thus, the lumen 140 is not in linear alignment with the lumens 104a and 104b. A retaining mechanism, such the pairs of detents 130a-130b (FIG. 2a) and their corresponding protrusions 156a-156b (FIG. 3b) keep the anchor 100 in the locked position.

It is important to note that various embodiments of the present invention can encompass various forms and still be within the scope of the attached or amended claims. For instance, in certain alternative embodiments, the buttresses 132a and 132b could be positioned on opposite sides of the longitudinal axis of the stationary member 112. The corresponding moveable member would then have a shape which essentially mirrors the moveable member 114. The functionality of such an alternative embodiment would be nearly identical to the embodiment discussed above except that rotation of moveable member 114 with respect to the stationary member is reversed. In other words, clockwise rotation of the moveable member would place the embodiment into a locked configuration and a counter clockwise rotation of the moveable member would place the alternative embodiment into an unlocked position.

Figure 5A:
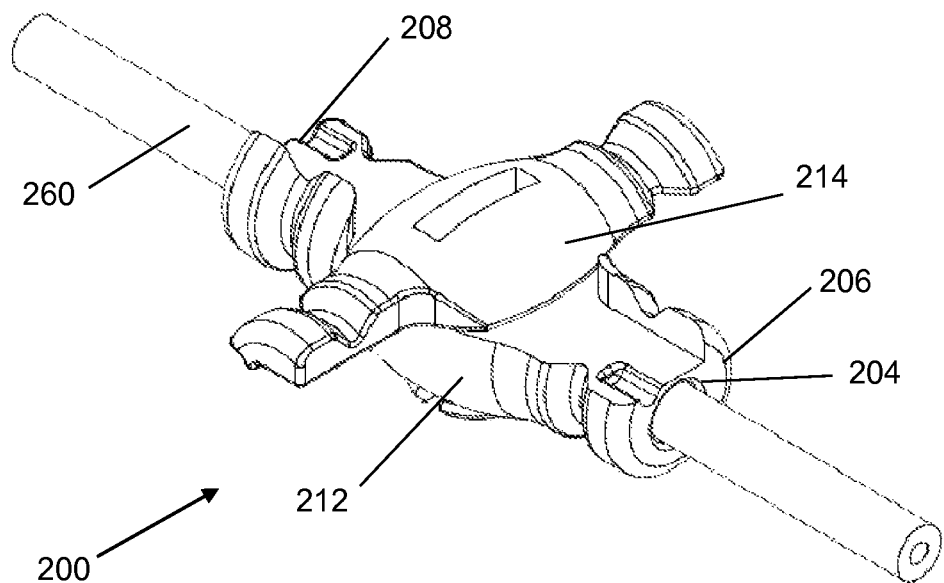
FIG. 5a is a perspective view of an alternative embodiment of an implantable anchor in an unlocked configuration.
Figure 5B:
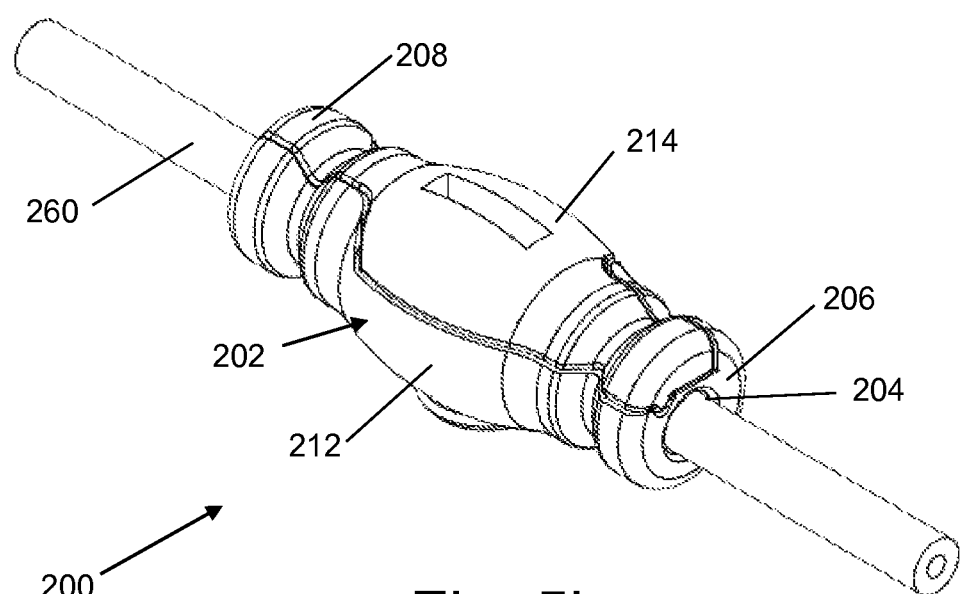
FIG. 5b is a perspective view of the anchor of FIG. 5a in locked configuration.

FIGS. 5a and 5b depict an implantable anchor 200 according to an alternative embodiment. The anchor 200 preferably functions in a manner similar to the anchor 100 and, hence, the internal components of the anchor 200 will not be discussed in as much detail. In general, the anchor 200 differs from the anchor 100 in the dimensional proportions of its respective members.

FIG. 5a depicts the anchor 200 in an open or unlocked configuration. FIG. 5b depicts the anchor 200 in a locked configuration.

The anchor 200 may comprise a longitudinal body 202 having one or more longitudinal lumens defined therein. In the illustrative embodiment, a lumen 204 runs longitudinally from a first or proximal end 206 to a second or distal end 208 of the longitudinal body 202. Although the lumen 204 is illustrated, any number of lumens may be used and are within the scope of the present invention. The diameter of the longitudinal lumen 204 may be sized to slidingly receive a lead 260. In use, therefore, the anchor 200 is intended to be placed on the proximal end of a lead 260 and slid over the lead until the anchor 200 is properly positioned along the lead.

Figure 6A:
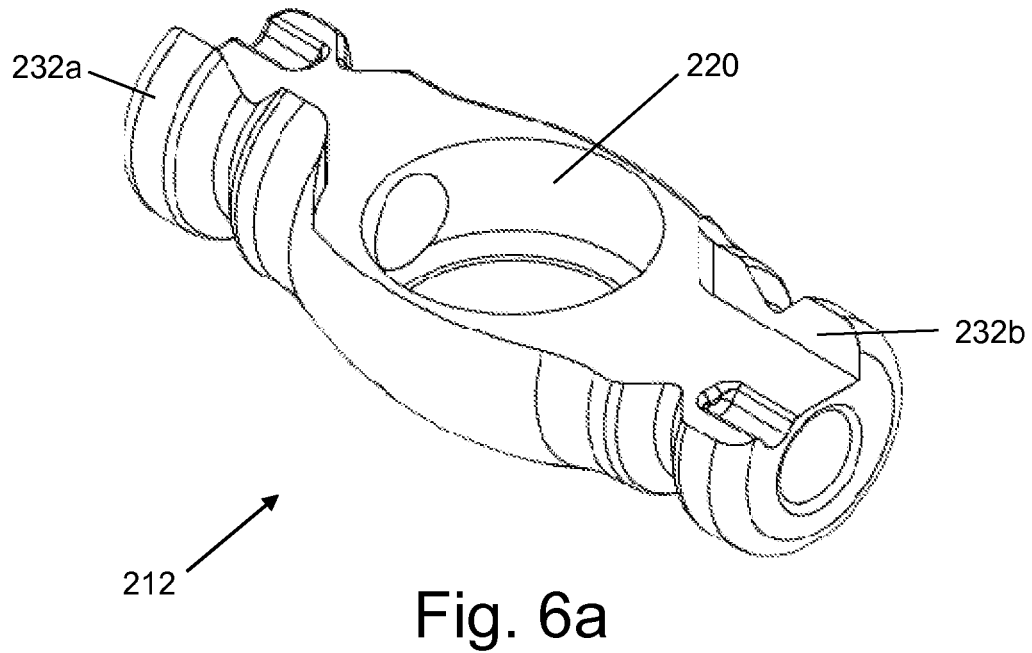
Figure 6B:
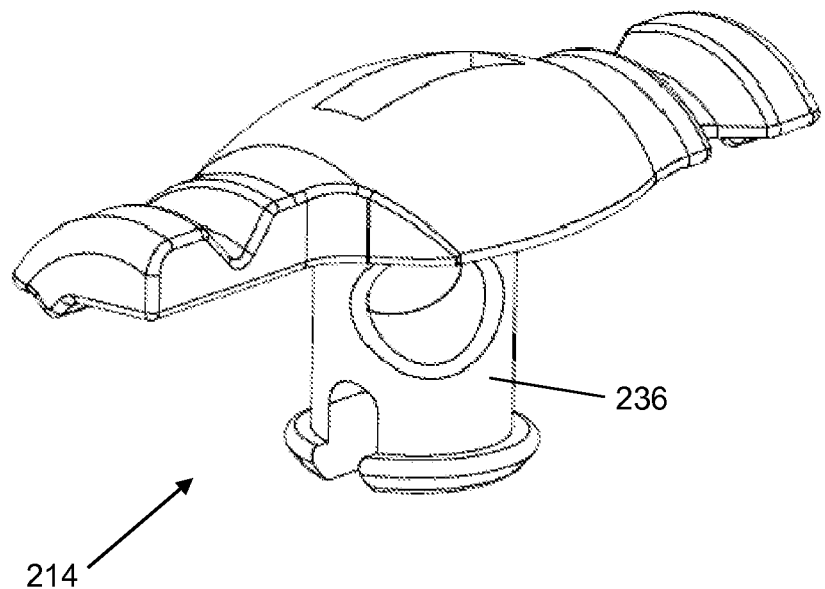

In certain embodiments, a moveable member 214 may be moveably coupled to a stationary member 212. The stationary member 212 is illustrated in greater detail in FIG. 6a. The moveable member 214 is illustrated in FIG. 6b. As noted above, the stationary member 212 is similar in function to the stationary member 112. The proportions and shape of the components are changed. For instance, the overall shape of the anchor 200 is more ellipsoid rather than cylindrical. Consequently, the buttresses 232a and 232b are proportionally smaller than the buttresses 132a and 132b, respectively.

In certain embodiments, the diameter of the circular opening 220 is larger in proportion to the stationary member 212. Similarly, the diameter of the transverse shaft 236 of the moveable member 214 has also been increased and other features have also been proportionally changed. Although the shape of the anchor 200 is different than the anchor 100, the operation of the anchor 200 is similar to the operation of the anchor 100. Reference should be made to anchor 100 for the operation of the anchor.

In certain embodiments, the anchor 100 and/or the anchor 200 may be fabricated using any suitable polymer processing technique. The polymer or polymers selected for the anchors 100 and 200 are preferably adapted for long term implantation. Biocompatibility and biostability are characteristics for the polymer selection for anchors 100 and 200. Also, the polymer preferably possesses a medium to high durometer to maintain the structural characteristics of the anchor 100 and 200. An example of a suitable polymer is polyetheretherketone (PEEK), although any biostable, biocompatible polymer having a suitable durometer and a suitable coefficient of friction can be employed.

Figure 7A:
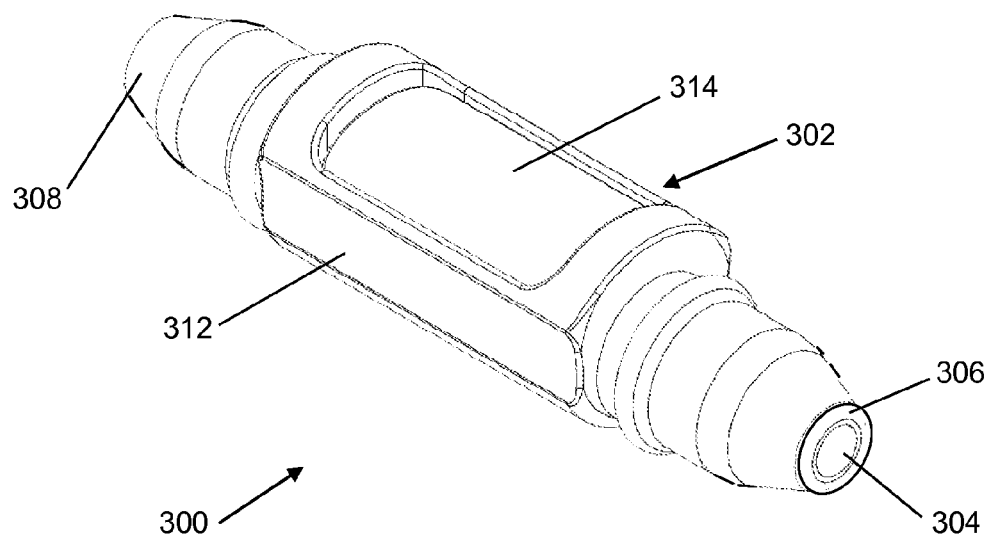
FIG. 7a is a perspective view of an alternative embodiment of an implantable in a first or unlocked configuration.
Figure 7B:
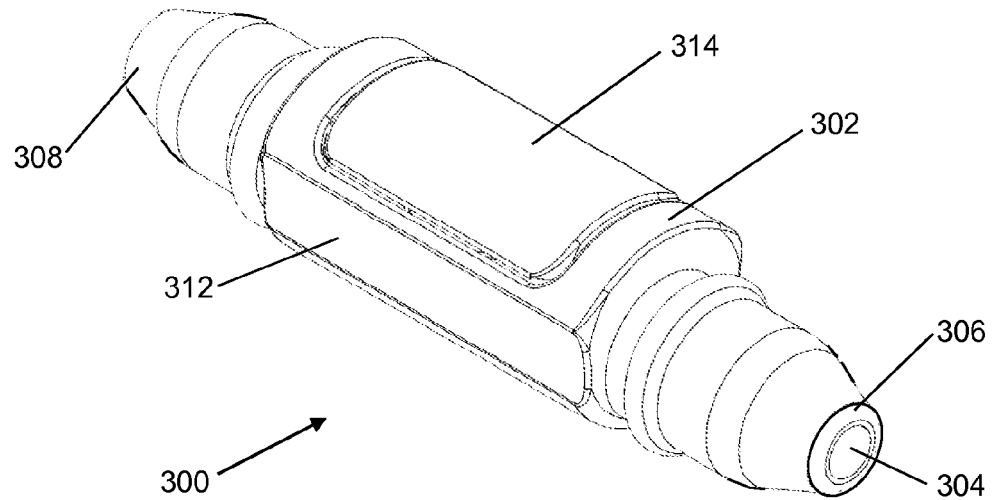
FIG. 7b is a perspective view of the anchor of 7a in a second or locked configuration.

FIG. 7a depicts an alternative embodiment of an implantable anchor 300 in a first or unlocked configuration. FIG. 7b depicts the anchor 300 in a second or locked configuration.

The anchor 300 may comprise a longitudinal body 302 having one or more longitudinal lumens defined therein. In the unlocked configuration, a lumen 304 runs longitudinally along a straight axis (i.e. linearly) from a first end 306 to a second end 308 of the longitudinal body 302. Although the lumen 304 is illustrated, any number of lumens may be used and are within the scope of the present invention. In use, therefore, one end of a lead (such as the proximal end) is intended to be threaded through the lumen 304. The anchor 300 is then slid over the lead or leads until the anchor is properly positioned along the longitudinal length of the lead or leads.

As illustrated in FIGS. 7a and 7b, the longitudinal body 302 includes two main portions: a stationary member 312 and a moveable or moveable member 314. As will be explained in detail later, when the moveable member 314 is in the unlocked position or configuration relative to the stationary member 312, a lead may be able to freely slide through the longitudinal lumen 304 (which is generally linear). When the moveable member 314 is in the locked position or configuration, as illustrated in FIG. 7b, the lumen 304 is no longer linear and the flexible lead is forced to bend or kink within the anchor 300. This bending substantially inhibits the lead from freely sliding through the longitudinal lumen 304 and locks the anchor 300 longitudinally in place relative to the lead.

Figure 8A:
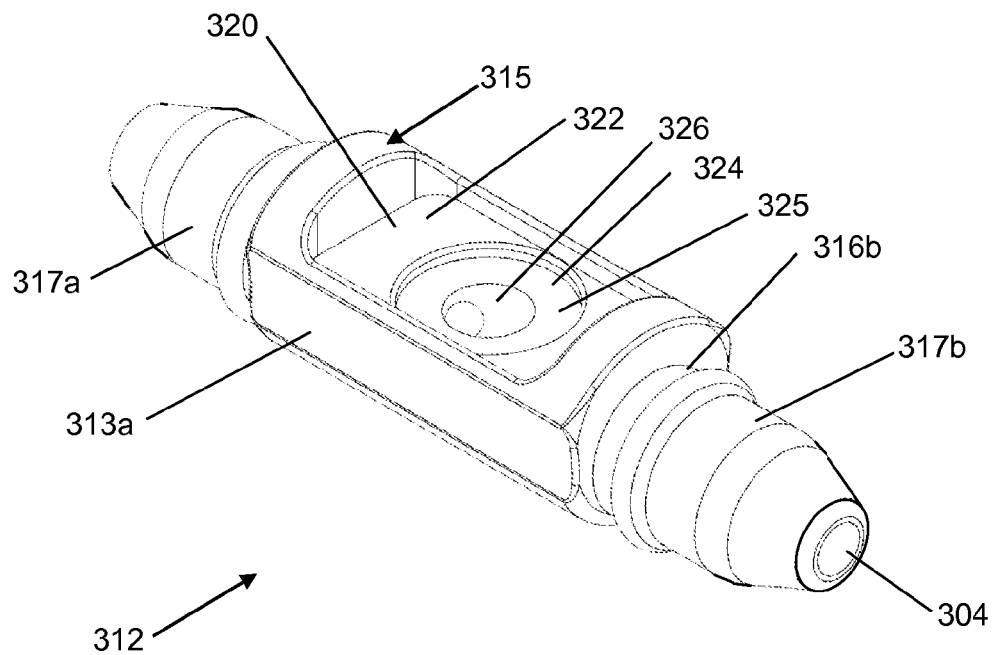
Figure 8B:
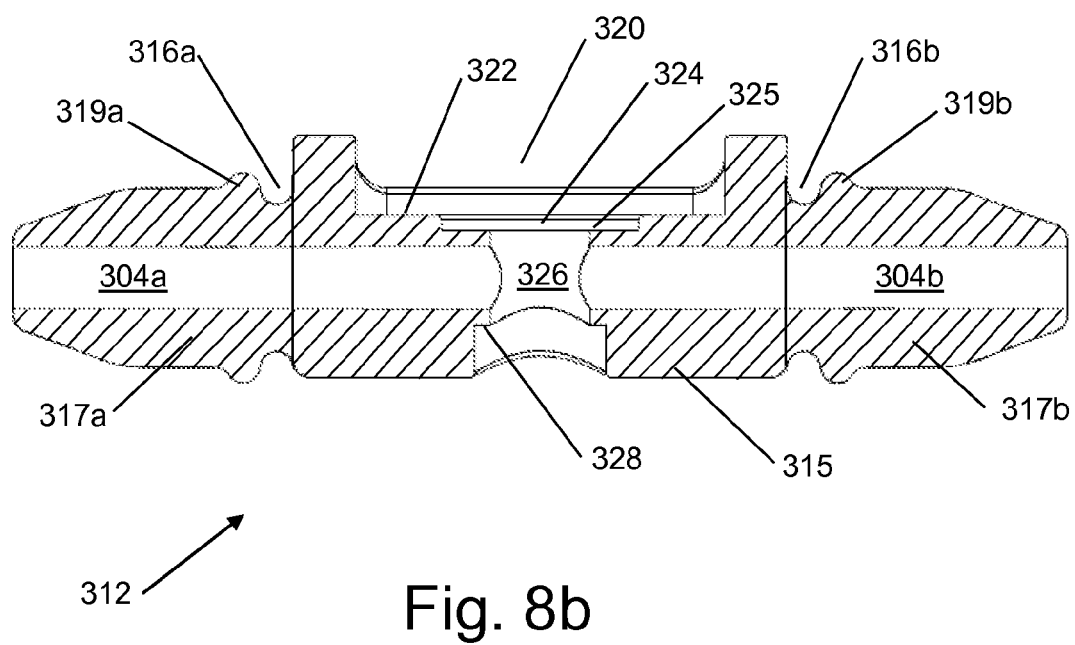

Turning now to FIG. 8a, there is illustrated the stationary member 312 of the anchor 300. FIG. 8b is a sectional view of the stationary member 312. In this embodiment, the stationary member 312 is partially cylindrical in shape having flat side surfaces on both sides, such as flat side surface 313a defined on the surface a center portion 315. End portions 317a and 317b extends longitudinally outwardly from the center portion 315. In some embodiments, the end portions 317a and 317b are generally cylindrical in shape and become conical in shape at their extreme ends.

In some embodiments, there is be defined circumferential indents or grooves 316a and 316b defined within the exterior wall portions of the end portions 317a and 317b, respectively. In certain embodiments, annular ribs 319a and 319b are formed adjacent to the circumferential grooves 316a and 316b. The circumferential grooves 316a, 316b and annular ribs 319a, 319b are designed to assist suturing of the anchor 300 to tissue of the patient by allowing a portion of the suture to fit around and within the circumferential grooves 316. In other embodiments, one or more anchor holes or other similar structures (such as additional groove or ribs) could also be provided.

Figure 9:
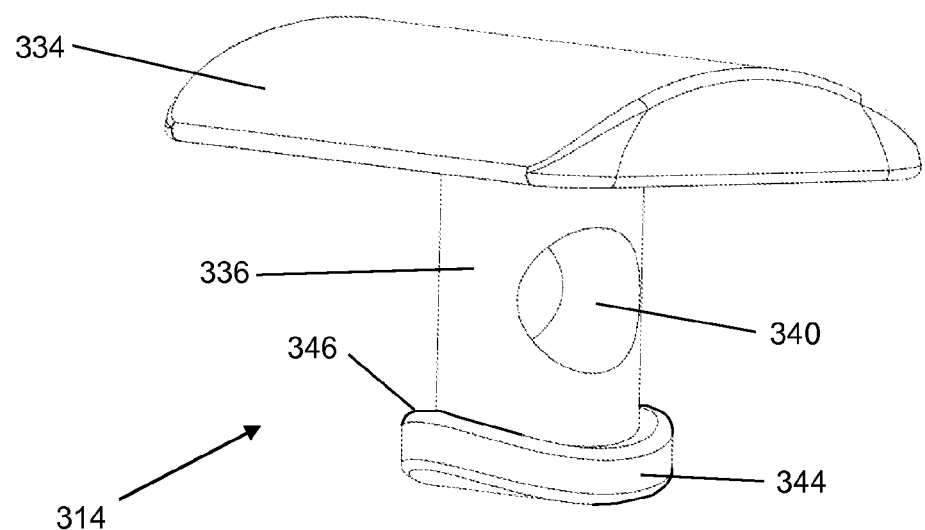
FIG. 9 is a perspective view of one embodiment of a component of the anchor of taken from a side of the member.

In certain embodiments, a transverse, generally rectangular side opening 320 is defined within the stationary member 312. As will be explained later, the side opening 320 is designed to receive a portion of the moveable member 314 (FIG. 9). A flat surface 322 defines the bottom of the side opening 320.

In certain embodiments, a circular opening 324 is defined within the flat surface 322. The circular opening 324 extends from the flat surface 322 to a predetermined depth to form a surface or shelf 325. As will be explained in detail below, in certain embodiments, the circular opening 324 is sized to act as a housing void for a biasing mechanism. In the illustrative embodiment, a transverse bore 326 is defined within the shelf 325 and extends entirely through the stationary member 312 and is transverse to the longitudinal axis of the stationary member 312 and the lumen 304. The bore 326 also bisects the longitudinal lumen 304 to form two lumens 304a and 304b which are longitudinally or linearly aligned with each other. Below the intersection with the lumen 304, the bore 326 abruptly expands to form an annular shelf 328.

Similar to the anchors 100 and 200 discussed above, the stationary member 312 of the anchor 300 may be fabricated using any suitable polymer processing technique. An example of a suitable polymer for the stationary member 312 is PEEK, although any biostable, biocompatible polymer having a suitable durometer and a suitable coefficient of friction can be employed.

In other embodiments, a combination of a relatively hard and soft (or flexible) material may be utilized to produce the stationary member 312. In such an embodiment, the central portion 315 (FIG. 8) may be made from a relatively hard material, such as PEEK and end portions 317a and 317b are fabricated from a more compliant material with a lower durometer value, such as silicone. Thus, in certain alternative embodiments, the end portions 317a and 317b are relatively flexible when compared to the central portion 315 and may act as strain relief ports with respect to the central portion 315.

FIG. 9 is a perspective view of the moveable member 314 taken from the side of the member. As illustrated, in certain embodiments the moveable member 314 comprises an actuating member 334. In certain embodiments, the actuating member 334 has a curved exterior surface which generally matches the cylindrical surface of the stationary member 312. A transverse shaft 336 protrudes from a flat surface (not shown) of the actuating member 334 to generally form a T-member.

The actuating member 334 is sized to fit and transversely travel within the side opening 320 of the stationary member 312. The transverse shaft 336 is sized to fit and travel within the transverse bore 326 (FIG. 8b) of the stationary member 312. A lumen or bore 340 runs through the transverse shaft 336. The lumen is sized to receive a lead of neuromuscular stimulation or drug delivery system. In certain embodiments, the lumen 340 is slightly beveled near the surface of the transverse shaft to form a guide or beveled edge to allow for easier threading of the lead (not shown) through the lumen. In this embodiment, the lumen 340 is generally parallel to the lumens 304a and 304b when the anchor 300 is in both the unlocked and locked configurations. However, the lumen 340 is only linearly aligned with the lumens 304a and 304b when the anchor 300 is in an unlocked configuration.

A lip 344 is formed on the end of the shaft 336 and has an upper edge 346. The lip 344 is curved in shape to match the curved surface of the stationary member 312. In operation, when the moveable member 314 is coupled with the stationary member 312, the upper edge 346 of the lip 344 abuts the annular shelf 328 (FIG. 8b) of the stationary member 312 to prevent the shaft 336 from sliding out of the transverse bore 326 of the stationary member.

Similar to the moveable member 114 discussed above, the moveable member 314 of the anchor 300 may be fabricated using any suitable polymer processing technique and may be fabricated out of any appropriate material, such as PEEK.

Figure 10:
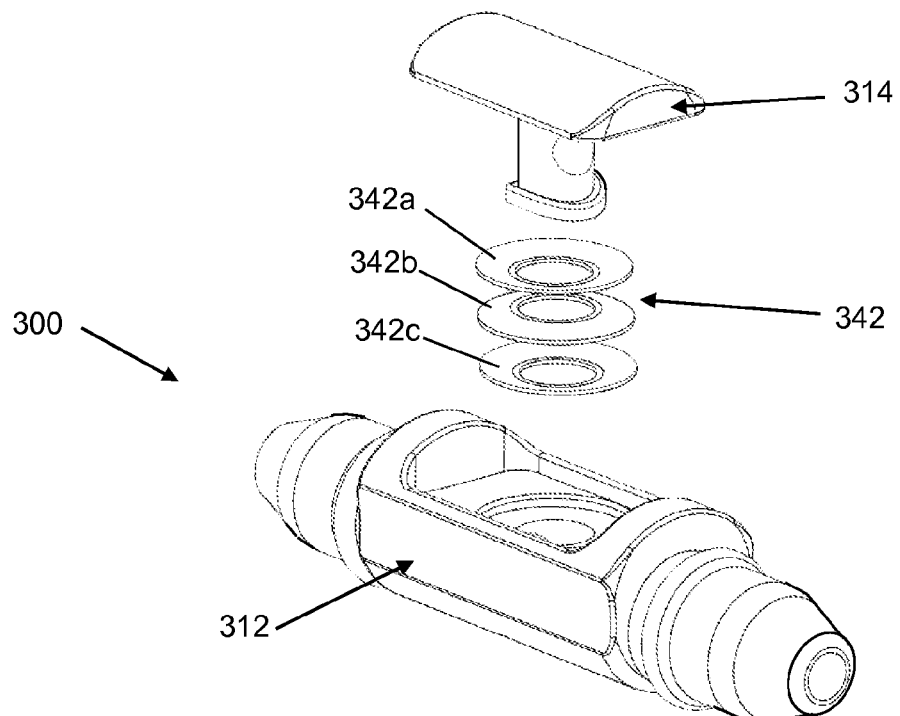
FIG. 10 is a perspective exploded view of the anchor of FIG. 7a illustrating the primary components.

Turning now to FIG. 10, there is presented an axonometric exploded view of the anchor 300. In this embodiment, there is illustrated the moveable member 314, the stationary member 312, and a biasing mechanism 342. The biasing mechanism 342 can be any appropriate biasing mechanism, including helical springs or leave springs. A plurality of three spring washers 342a-342c stacked in series is illustrated in this embodiment.

The inner diameter of the spring washers 342a-342c is sized to sildeably fit around the transverse shaft 336. The outer diameter of the spring washers 342a-342c is sized to fit within the circular opening 324 (FIGS. 8a, and 8b) such that the spring washers have enough clearance within the circular opening to easily deflect when actuated.

Figure 11A:
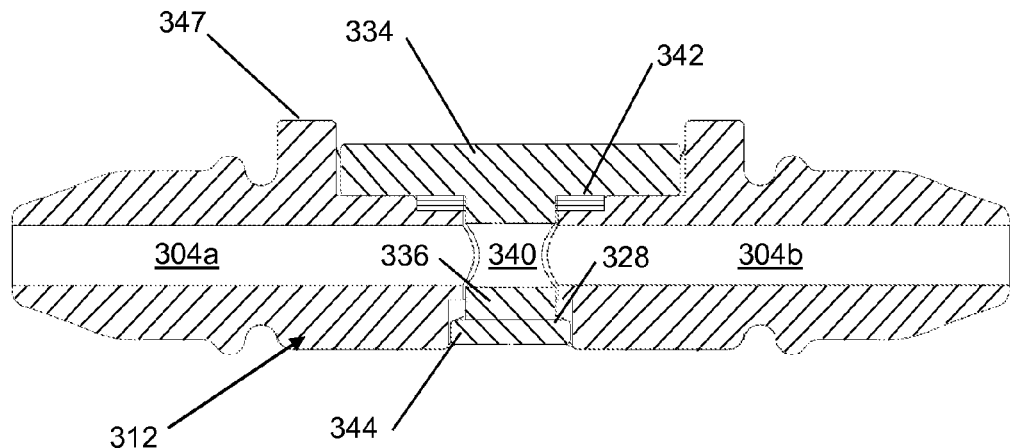
FIG. 11a is a sectional view of the anchor of FIG. 7a in an unlocked position or configuration.
Figure 11B:
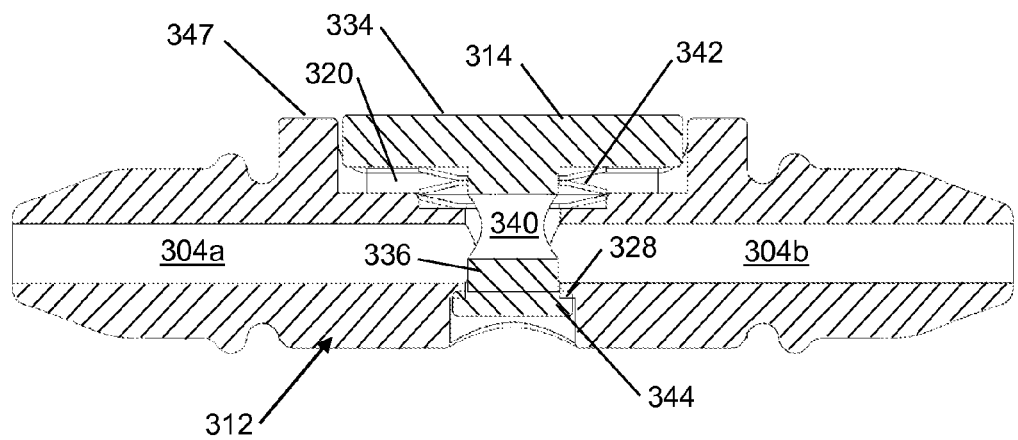
FIG. 11b is a sectional view of the anchor of FIG. 7a in a locked configuration.
Figure 12A:
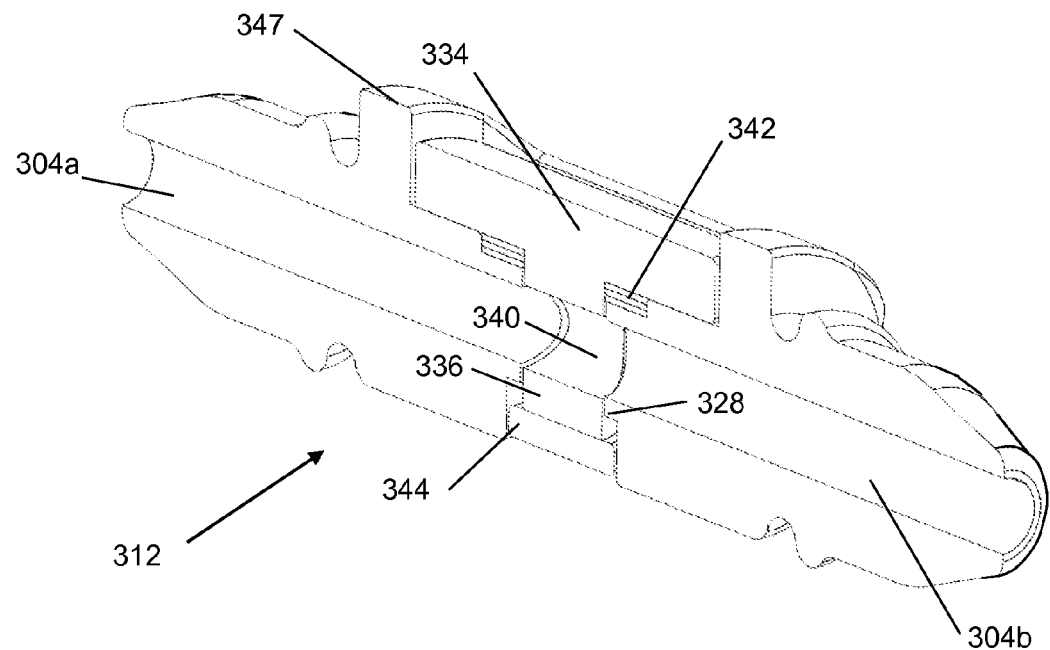
FIG. 12a is a perspective sectional view of the anchor of FIG. 7a in an unlocked position or configuration.
Figure 12B:
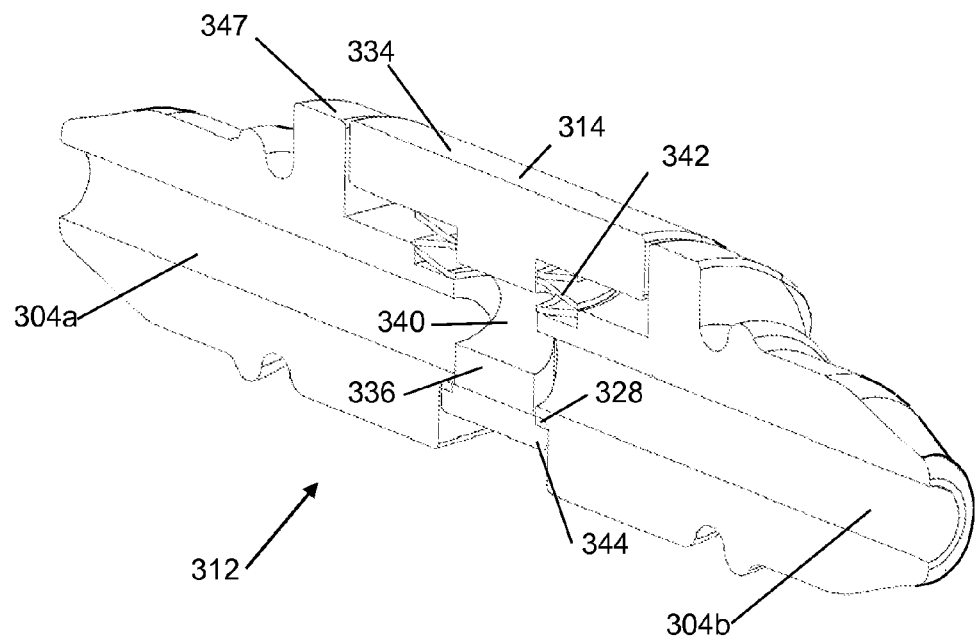
FIG. 12b is a perspective sectional view of the anchor of FIG. 7a in a locked position or configuration.

Turning now to FIG. 11a, there is illustrated a sectional view of the anchor 300 in an unlocked position or configuration. FIG. 11b illustrates a sectional view of the anchor 300 in a locked configuration. Similarly, FIG. 12a is a sectional view of the anchor 300 in an unlocked position or configuration. FIGS. 11a and 12a correspond to the unlocked configuration presented in FIG. 7a. FIGS. 11b and 12b correspond to locked configuration of FIG. 7b.

In use, the anchor 300 is normally biased in a locked configuration as illustrated in FIG. 11b and FIG. 12b. In this configuration, the lumens 304a and 304b of the stationary member 312 are not aligned with the lumen 340 of the moveable member 314. As illustrated, the biasing mechanism 342 (such as spring washers 342a-342b) biases or pushes against the actuating member 334. This biasing force keeps the exterior curved surface of the actuating member 334 generally flush with the exterior surface 347 of the stationary member 312 as illustrated in FIGS. 11b and 12b. In this locked configuration, the lip 344 of the shaft 336 abuts the shelf 328 of the stationary member 312 and prevents the biasing mechanism 342 from pushing the actuating member 334 entirely out of the side opening 320. Because the lumen 340 is not linearly aligned with the lumens 304a and 304a, a lead cannot be threaded through the anchor 300 in this locked configuration.

In order to unlock the anchor, a user (such as a surgeon) depresses the actuating member 334 which overcomes the upward biasing force of the biasing mechanism 342. When the actuating member 334 is fully depressed, the lumen 340 of the moveable member 314 is now linearly aligned with the lumens 304a and 304b of the stationary member as illustrated in FIGS. 11a and 12a. The user can switch between the locked and unlocked configuration simply by pressing or releasing the actuating member 334.

The diameters of the lumens 304a, 304b, and 340 are sufficiently large to permit the introduction of a lead with little difficulty. Thus, when the moveable member 314 is in the unlocked position, the anchor 300 may be freely moved along the lead. Once the anchor 300 is in the proper longitudinal position with respect to the lead, the user can simply release the actuating member 334. When the actuating member 334 is released (i.e., no longer depressed by the user), the biasing mechanism 342 will exert a force on the actuating member. This biasing force will push the actuating member 334 (and the shaft 336 along with the lumen 340) up so that the lumen 340 is no longer linear with the lumens 304a and 304b. When the lumen 340 is repositioned, then any portion of a lead which may be positioned in the lumen 340 will also travel—thus causing a bending or kinking of the lead. In certain embodiments, two bends or curves will be introduced in the lead as the lead is pulled out of linear alignment by the lumen 340. The lead, therefore, is substantially inhibited from slipping through the anchor 300 along its longitudinal axis. The biasing mechanism 342 also retains the lumen 340 out of linear alignment with the lumens 304a and 304b. Thus, functioning as a retaining mechanism for the anchor 300.

Anchors according to representative embodiments discussed above may be utilized in conjunction with any suitable implantable medical device that comprises an implantable lead. For example, anchors 100 through 300 can be utilized to anchor a stimulation lead of a neurostimulation system as shown in FIG. 13. A neurostimulation system 400 includes a pulse generator 402 and one or more stimulation leads 404. An example of a commercially available pulse generator is the EON™ pulse generator available from St. Jude Medical. An example of a commercially available stimulation lead is the Quattrode™ lead available from St. Jude Medical.

The pulse generator 402 is typically implemented using a metallic housing that encloses circuitry for generating the electrical pulses for application to neural tissue of the patient. The pulse generator 402 is usually implanted within a subcutaneous pocket created under the skin by a physician. The lead 404 is used to conduct the electrical pulses from the implant site of the pulse generator for application to the targeted nerve tissue via electrodes 406. The lead 404 typically includes a lead body of an insulative polymer material with embedded wire conductors extending through the lead body. The electrodes 406 of the lead body are coupled to the conductors to deliver the electrical pulses to the nerve tissue. For example, the distal end 408 of lead 404 may be positioned within the epidural space of the patient to deliver electrical stimulation to spinal nerves to treat chronic pain of the patient. The anchors 100 through 300, such as anchor 100, may be utilized to ensure that the distal end 408 of the lead 404 remains adjacent to the appropriate nerves associated with the chronic pain of the patient. In some embodiments, an "extension" lead (not shown) may be utilized as an intermediate connector if deemed appropriate by the physician.

In certain embodiments of spinal cord stimulation systems, the lead 404 is a "body compliant" lead that possesses mechanical characteristics that allow the lead 404 to stretch in response to forces experienced with the patient's body. For example, the lead 404 may be adapted to stretch up to 25% in response to low stretching forces such as 2-2 pounds of force. The ability to exhibit significant elongation in response to such low forces enables the lead to be relatively robust (e.g., does not experience significant conductor breakage). The anchors 100-300 are especially useful when used in conjunction with body compliant leads because the anchors will hold the leads in position even if the lead diameters are reduced.

Figure 14:
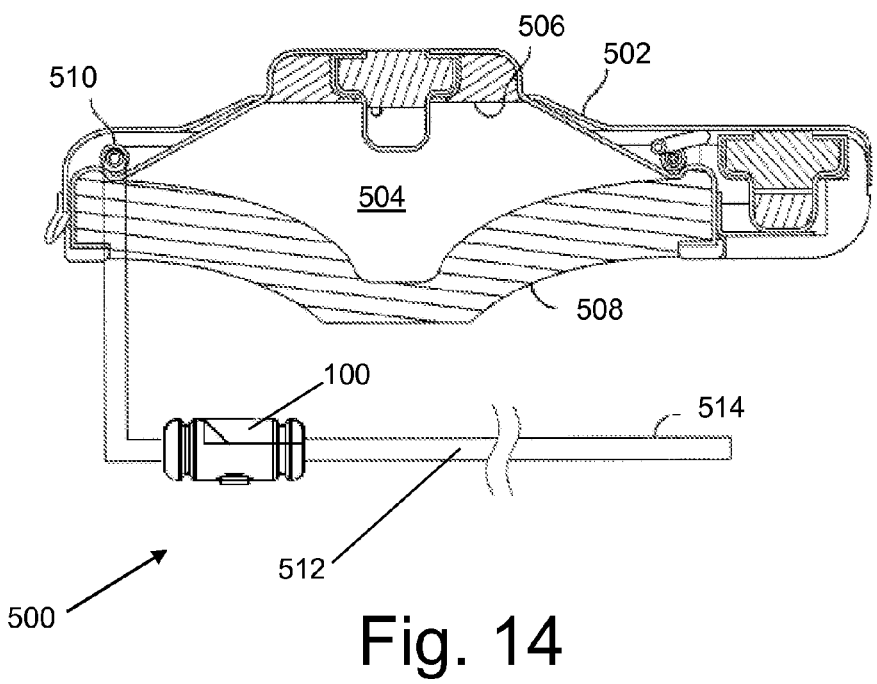
FIG. 14 is a diagram illustrating an implantable drug infusion system using one embodiment of the above anchors.

Alternatively, some embodiments of the anchors 100 through 300 can be utilized to anchor an infusion catheter of an implantable drug infusion device 500 as shown in FIG. 14. The implantable infusion drug pump device 500 may include a central housing 502, a reservoir 504 to hold the infusate, a septum 506 to allow infusate to be introduced into the reservoir, an energy source 508 (e.g., a spring diaphragm) to drive the infusate from the reservoir and through an outlet port 510, and various flow control elements (not shown).

The central housing 502 of the device is often implanted in a suitable subcutaneous region with the septum 506 positioned immediately below the skin of the patient to facilitate access to the reservoir 504 for refilling purposes. A catheter 512 is attached to the outlet port 510 of the central housing 502 to receive the infusate outflow. A distal end 514 of the catheter is implanted within the patient adjacent to the appropriate therapy site. The anchors 100 through 300, such as the anchor 100, may be utilized to ensure that the distal end 514 of the lead 512 remains adjacent to the appropriate site generating the chronic pain of the patient.

Thus, the anchors described in this specification may be used with a wide variety of medical treatment systems, such as neurostimulation systems. The anchors are designed to hold the leads in place even if their exterior diameters are reduced during implantation or patient use. The anchors are simple to operate and allow the user to position or reposition the anchors along the leads as desired. Furthermore, the anchors bend and retain the leads at a precise predetermined angle (or angles). Certain embodiments have stops or other structure devices in place so that a user cannot twist the lead beyond the predetermined angle.

Although some representative embodiments have been discussed in terms of anchoring intrathecal and epidural catheters and leads, anchors can be employed according to alternative embodiments for any suitable location. For example, an anchor according to some embodiments could be used for peripheral nerve stimulation and gastric pacing applications.

In another example, there may be an implantable suturing anchor comprising: a body having a longitudinal lumen defined therein, wherein the lumen is sized to accept a portion of a medical lead; a bending mechanism coupled to body for bending the lead to a predetermined angle within the body, a retaining mechanism coupled to the bending mechanism for maintaining the predetermined angle of the bent lead within the body.

In another example, there may be a suturing anchor comprising: an anchor body, a first lumen defined within the anchor body, a moveable member coupled to the anchor body, a second lumen defined within the moveable member wherein in a unlocked configuration, the second lumen is longitudinally aligned with the first lumen and in a locked configuration, the second lumen is not aligned with the first lumen.

In the above example, there may also be a third lumen defined within the anchor body and longitudinally aligned with the first lumen.

In the above example, the moveable member may be rotatably coupled to the anchor body such that the moveable member rotates from a first position where the first and second lumens are aligned with a third lumen to a second position where the first and second lumens are not aligned with the third lumen.

In some embodiments, there may be a medical method for anchoring a surgical anchor to a lead, the method comprising threading a lead through a substantially straight longitudinal lumen of a suturing anchor, longitudinally positioning a suturing anchor along the lead, bending the longitudinal lumen of the suturing anchor to a predetermined angle such that the longitudinal lumen is no longer straight thereby bending the lead such that the lead is prevented from longitudinally moving with respect to the anchor. Additional embodiments may include the step of retaining the bending of the longitudinal lumen to keep the anchor position locked with respect to the lead.

Although representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure that processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

Any combination of the features discussed above are within the scope of certain embodiments of the present invention. Thus, a feature disclosed in reference to one embodiment may be combined with another embodiment. Furthermore, combinations of disclosed features and alternative features are within the scope of certain embodiments of the present invention.

The abstract of the disclosure is provided for the sole reason of complying with the rules requiring an abstract, which will allow a searcher to quickly ascertain the subject matter of the technical disclosure of any patent issued from this disclosure. It is submitted with the understanding that it will not be used to interpret or limit the scope or meaning of the claims.

What is claimed is:

1. An implantable anchor for anchoring a medical lead or a catheter, the anchor comprising:
   a stationary member including,
      a first lumen having a longitudinal axis and defined within the stationary member,
      a second lumen defined within the stationary member and linearly aligned with the first lumen,
      a first surface defined on the stationary member,
      an opening defined in the first surface having a center axis which is transverse to the longitudinal axis of the first lumen,
      a first strain relief portion having a first strain relief lumen longitudinally aligned with the first lumen,
      a second strain relief portion having a second strain relief lumen longitudinally aligned with the second lumen,
      a center portion housing the first lumen and the second lumen and coupled to the first strain relief portion on a first end and coupled to the second strain relief portion on a second end, and wherein the first strain relief portion and the second strain relief portion are formed from a first material and the center portion is formed from a second material, and the first material is flexible relative to the second material, a moveable member rotatably coupled to the stationary member, wherein the moveable member includes a second surface opposing the first surface, a shaft projecting from the second surface and sized to be partially housed in the opening, a third lumen defined within the shaft, and wherein when the moveable member can rotate with respect to the stationary member from an unlocked configuration where the third lumen is linearly aligned with the first and second lumens to a locked configuration wherein the third lumen is not linearly aligned to the first lumen.

2. The implantable anchor of claim 1, further comprising a retaining mechanism defined within the moveable member and the stationary member to keep the moveable member in the locked configuration.

3. The implantable anchor of claim 2, wherein the retaining mechanism comprises at least one detent defined in the first surface of the stationary member and at least one protrusion projecting from the second surface of the moveable member sized to mate with the at least one detent.

4. The implantable anchor of claim 1, further comprising at least one stop coupled to the stationary member to limit rotation of the moveable member with respect to the stationary member.

5. The implantable anchor of claim 1, further comprising an engagement feature defined in an exterior surface of the moveable member sized to receive an instrument for applying torque to rotate the moveable member.

6. The implantable anchor of claim 1, further comprising at least one annular groove defined on the exterior surfaces of the stationary member and the moveable member for receiving a portion of a suture.

7. The implantable anchor of claim 1, further comprising a first curved groove defined on an exterior surface of the stationary member and a second curved groove defined on an exterior surface of the moveable member, wherein the first curved groove and second curved grooved are aligned and form a circumferential groove when the anchor is in the locked configuration.

8. The implantable anchor of claim 1, wherein the moveable member rotates about an axis which is generally transverse to the longitudinal axis of the first lumen.

9. An implantable anchor comprising:
a stationary body including:
a first lumen defined within the stationary body,
a second lumen defined within the stationary body wherein the second lumen is longitudinally aligned with the first lumen,
a first strain relief portion having a first strain relief lumen longitudinally aligned with the first lumen,
a second strain relief portion having a second strain relief lumen longitudinally aligned with the second lumen,
a center portion housing the first lumen and the second lumen and coupled to the first strain relief portion on a first end and coupled to the second strain relief portion on a second end, and
wherein the first strain relief portion and the second strain relief portion are formed from a first material and the center portion is formed from a second material, and the first material is flexible relative to the second material,
a moveable member slidingly engaging the stationary body having a third lumen, wherein in a unlocked configuration the third lumen is longitudinally aligned with the first and second lumens and in a locked configuration the third lumen is not longitudinally aligned with the second lumen, and
a biasing mechanism coupled to the stationary body and the moveable member wherein the biasing mechanism biases the moveable member into the locked configuration with respect to the stationary body.

10. The implantable anchor of claim 9, wherein the biasing mechanism comprises a spring.

11. The implantable anchor of claim 9, wherein the biasing mechanism comprises a series of spring washers.

12. The implantable anchor of claim 9, wherein the moveable member comprises an actuating surface and a shaft protruding from a second surface of the moveable member such that the shaft is generally perpendicular to a longitudinal axis of the third lumen.

13. The implantable anchor of claim 12, wherein the stationary body further comprises a transverse opening sized to house the shaft such that the shaft can travel a predetermined distance within the transverse opening.

14. The implantable anchor of claim 12, wherein the third lumen is defined within the shaft and is generally parallel to the longitudinal axis of the first lumen.

15. The implantable anchor of claim 12, further comprising a retaining feature defined on the surface of the shaft for retaining the shaft within the stationary body.

16. The implantable anchor of claim 9, further comprising one or more circumferential grooves defined in an exterior surface of the stationary member for retaining a portion of a suture.

17. The implantable anchor of claim 9, further comprising one or more annular ribs projecting from an exterior surface of the stationary member for retaining a portion of a suture.

* * * * *